US009724076B2

(12) United States Patent
Fiebig et al.

(10) Patent No.: US 9,724,076 B2
(45) Date of Patent: Aug. 8, 2017

(54) BIOPSY DEVICE VALVE ASSEMBLY

(71) Applicant: Devicor Medical Products, Inc., Cincinnati, OH (US)

(72) Inventors: Kevin M. Fiebig, Cincinnati, OH (US); John A. Hibner, Mason, OH (US); Andrew P. Nock, Centerville, OH (US); John R. Andrisek, Liberty Township, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 656 days.

(21) Appl. No.: 13/765,931

(22) Filed: Feb. 13, 2013

(65) Prior Publication Data

US 2013/0218047 A1   Aug. 22, 2013

Related U.S. Application Data

(60) Provisional application No. 61/598,939, filed on Feb. 15, 2012.

(51) Int. Cl.
*A61B 10/00* (2006.01)
*A61B 10/02* (2006.01)

(52) U.S. Cl.
CPC ...... *A61B 10/0283* (2013.01); *A61B 10/0266* (2013.01); *A61B 10/0275* (2013.01)

(58) Field of Classification Search
CPC ............ A61B 10/0283; A61B 10/0275; A61B 10/0208
USPC ......................................... 600/562, 564, 566
See application file for complete search history.

(56) References Cited

U.S. PATENT DOCUMENTS

| 5,526,822 | A |   | 6/1996  | Burbank et al. |
|-----------|---|---|---------|----------------|
| 6,017,316 | A |   | 1/2000  | Ritchart et al. |
| 6,086,544 | A |   | 7/2000  | Hibner et al. |
| 6,120,462 | A | * | 9/2000  | Hibner ............... A61B 10/0275 600/566 |
| 6,162,187 | A |   | 12/2000 | Buzzard et al. |

(Continued)

FOREIGN PATENT DOCUMENTS

CN   1754514 A   4/2006

OTHER PUBLICATIONS

U.S. Appl. No. 13/205,189, filed Aug. 8, 2011, Fiebig et al.

(Continued)

*Primary Examiner* — Daniel Cerioni
(74) *Attorney, Agent, or Firm* — Frost Brown Todd LLC

(57) ABSTRACT

A biopsy assembly includes a biopsy device, a vacuum source, and a valve assembly. The biopsy device includes a body, a needle extending distally from the body, and a cutter translatable relative to the needle. The needle includes a lateral tissue receiving aperture. The cutter is translatable to selectively close the lateral tissue receiving aperture of the needle. The valve assembly is in fluid communication with the needle. The valve assembly includes a first valve, a second valve, and tubular member. Each of the first valve and the second valve selectively provide atmospheric venting or vacuum to the needle. The tubular member is coupled with the vacuum source and includes a first and second connector extending transversely from the tubular member. The first and second connectors couple to the first and second valves to provide vacuum to the first and second valves.

18 Claims, 14 Drawing Sheets

(56) References Cited

U.S. PATENT DOCUMENTS

| | | | |
|---|---|---|---|
| 6,273,862 | B1 | 8/2001 | Privitera et al. |
| 6,626,849 | B2 | 9/2003 | Huitema et al. |
| 7,442,171 | B2 | 10/2008 | Stephens et al. |
| 7,575,556 | B2 | 8/2009 | Speeg et al. |
| 7,662,109 | B2 | 2/2010 | Hibner |
| 7,854,706 | B2 | 12/2010 | Hibner |
| 7,938,786 | B2 | 5/2011 | Ritchie et al. |
| 8,118,755 | B2 | 2/2012 | Hibner et al. |
| 8,206,316 | B2 | 6/2012 | Hibner et al. |
| 8,938,285 | B2 | 1/2015 | Fiebig et al. |
| 2005/0085838 | A1* | 4/2005 | Thompson ......... A61B 10/0275 606/170 |
| 2006/0074345 | A1 | 4/2006 | Hibner |
| 2008/0146962 | A1 | 6/2008 | Ritchie et al. |
| 2008/0214955 | A1 | 9/2008 | Speeg et al. |
| 2009/0171242 | A1* | 7/2009 | Hibner ............... A61B 10/0275 600/566 |
| 2010/0113971 | A1 | 5/2010 | Hibner |
| 2010/0152610 | A1 | 6/2010 | Parihar et al. |
| 2010/0160819 | A1 | 6/2010 | Parihar et al. |
| 2011/0004119 | A1 | 1/2011 | Hoffa et al. |
| 2012/0109007 | A1 | 5/2012 | Rhad et al. |
| 2012/0265095 | A1 | 10/2012 | Fiebig |
| 2012/0310110 | A1 | 12/2012 | Rhad et al. |
| 2013/0053724 | A1 | 2/2013 | Fiebig et al. |

OTHER PUBLICATIONS

U.S. Appl. No. 13/218,656, filed Aug. 26, 2011, Fiebig et al.
U.S. Appl. No. 61/727,889, filed Nov. 19, 2012, Mescher.
International Search Report and Written Opinion dated May 29, 2013 for Application No. PCT/US2013/025853.
Chinese Office Action dated Dec. 3, 2015 for Application No. 201380005246.1.
Supplementary European Search Report and Written Opinion dated Sep. 16, 2015 for Application No. EP 13749571.
U.S. Appl. No. 61/727,889, filed Nov. 19, 2012.

\* cited by examiner

BIOPSY DEVICE VALVE ASSEMBLY

PRIORITY

This application claims priority to U.S. Provisional Patent Application Ser. No. 61/598,939, filed Feb. 15, 2012, entitled "Biopsy Device Valve Assembly," the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 11, 2003; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,938,786, entitled "Vacuum Timing Algorithm for Biopsy Device," issued May 10, 2011; U.S. Pat. No. 7,662,109, entitled "Biopsy Device with Replaceable Probe Incorporating Static Vacuum Source Dual Valve Sample Stacking Retrieval and Saline Flush," issued Feb. 16, 2010; U.S. Pat. Pub. No. 2006/0074345, entitled "Biopsy Apparatus and Method," published Apr. 6, 2006; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008, now patented as U.S. Pat. No. 8,118,755; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0317997, entitled "Tetherless Biopsy Device with Reusable Portion," published Dec. 16, 2010, now patented as U.S. Pat. No. 8,206,316; U.S. Non-Provisional patent application Ser. No. 12/953,715, entitled "Handheld Biopsy Device with Needle Firing," filed Nov. 24, 2010, published as U.S. Pat. Pub. No. 2012/0109007 on May 3, 2012; U.S. Non-Provisional patent application Ser. No. 13/086,567, entitled "Biopsy Device with Motorized Needle Firing," filed Apr. 14, 2011, published as U.S. Pat. Pub. No. 2012/0265095 on Oct. 18, 2012; U.S. Non-Provisional patent application Ser. No. 13/150,950, entitled "Needle Assembly and Blade Assembly for Biopsy Device," filed Jun. 1, 2011, published as U.S. Pat. Pub. No. 2012/0310110 on Dec. 6, 2012; U.S. Non-Provisional patent application Ser. No. 13/205,189, entitled "Access Chamber and Markers for Biopsy Device," filed Aug. 8, 2011; U.S. Non-Provisional patent application Ser. No. 13/218,656, entitled "Biopsy Device Tissue Sample Holder with Bulk Chamber and Pathology Chamber," filed Aug. 26, 2011; and U.S. Provisional Patent App. No. 61/727,889, entitled "Biopsy System with Graphical User Interface," filed Nov. 19, 2012. The disclosure of each of the above-cited U.S. patents, U.S. patent application Publications, U.S. Non-Provisional patent applications, and U.S. Provisional patent application is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
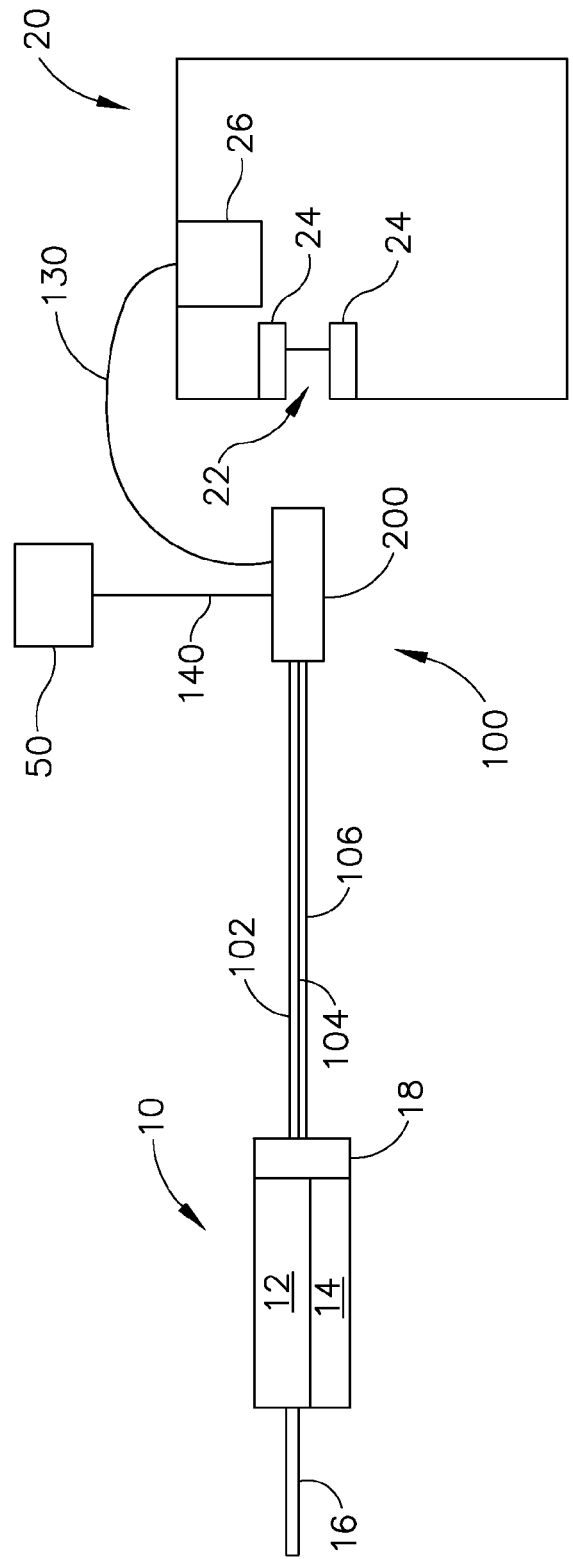
FIG. 1 depicts a schematic diagram showing an exemplary biopsy device, an exemplary control unit, an exemplary valve assembly unit, and a saline bag.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy Device

FIG. 1 depicts an exemplary biopsy device (10), an exemplary control unit (20), an exemplary valve assembly unit (100), and a saline bag (50). Saline bag (50) is fluidly coupled to valve assembly unit (100) to provide a source of saline to biopsy device (10), though this is merely optional. Biopsy device (10) of this example comprises a probe (12) and a holster (14). A needle (16) extends distally from probe (12), and is inserted into a patient's tissue to obtain tissue samples. The tissue samples are deposited in a tissue sample holder (18) at the proximal end of probe (12). It should also be understood that the use of the term "holster" herein should not be read as requiring any portion of probe (12) to be inserted into any portion of holster (14). For instance, probe (12) may be removably secured to holster (14) by a variety of structures, components, features, etc. (e.g., bayonet mounts, latches, prongs, clamps, clips, snap fittings, etc.). Furthermore, in some biopsy devices (10), probe (12) and holster (14) may be of unitary or integral construction, such that the two components cannot be separated. By way of example only, in versions where probe (12) and holster (14) are provided as separable components, probe (12) may be provided as a disposable component, while holster (14) may be provided as a reusable component. Still other suitable structural and functional relationships between probe (12) and holster (14) will be apparent to those of ordinary skill in the art in view of the teachings herein.

Figure 2:
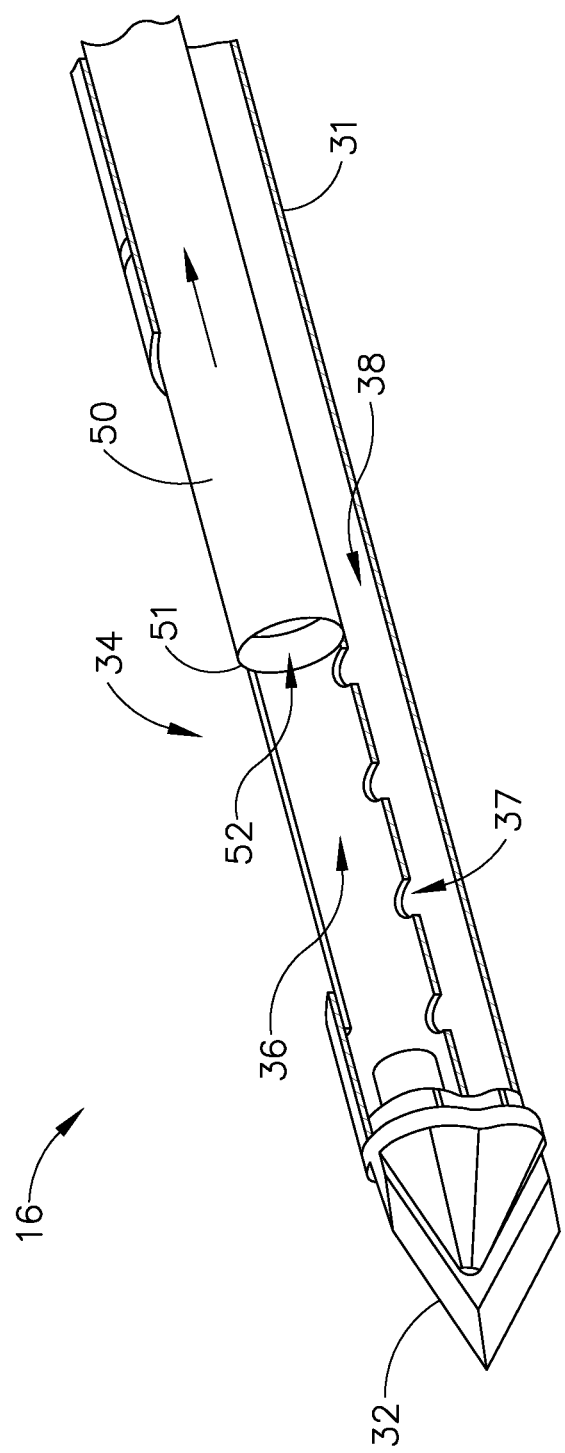
FIG. 2 depicts a perspective cross sectional view of a needle portion of the biopsy device of FIG. 1, with a cutter in a partially retracted position.

Needle (16) of the present example comprises a cannula (31) with a tissue piercing tip (32), a lateral aperture (34), a first lumen (36), and a second lumen (38), as shown in FIG. 2. Tissue piercing tip (32) is configured to pierce and penetrate tissue, without requiring a high amount of force, and without requiring an opening to be pre-formed in the tissue prior to insertion of tip (32). A cutter (50) is disposed in first lumen (36), and is operable to rotate and translate within first lumen (36). Lateral aperture (34) is located proximal to tip (32), is in fluid communication with first lumen (36), and is configured to receive tissue when needle (16) is inserted in a biopsy site and when cutter (50) is retracted. A plurality of openings (37) provide fluid communication between first and second lumens (36, 38). Cutter (50) of the present example is substantially hollow, such that cutter (50) defines a cutter lumen (52). Cutter (50) also has a substantially sharp distal edge (51), such that cutter (50) is operable to sever a biopsy sample from tissue protruding through lateral aperture (34) of needle (16).

Biopsy device (10) may be further constructed in accordance with at least some of the teachings of U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 11, 2003; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,938,786, entitled "Vacuum Timing Algorithm for Biopsy Device," issued May 10, 2011; U.S. Pat. Pub. No. 2006/0074345, entitled "Biopsy Apparatus and Method," published Apr. 6, 2006; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008, now patented as U.S. Pat. No. 8,118,755; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0317997, entitled "Tetherless Biopsy Device with Reusable Portion," published Dec. 16, 2010, now patented as U.S. Pat. No. 8,206,316; U.S. Non-Provisional patent application Ser. No. 12/953,715, entitled "Handheld Biopsy Device with Needle Firing," filed Nov. 24, 2010, published as U.S. Pat. Pub. No. 2012/0109007 on May 3, 2012; U.S. Non-Provisional patent application Ser. No. 13/086,567, entitled "Biopsy Device with Motorized Needle Firing," filed Apr. 14, 2011, published as U.S. Pat. Pub. No. 2012/0265095 on Oct. 18, 2012; U.S. Non-Provisional patent application Ser. No. 13/150,950, entitled "Needle Assembly and Blade Assembly for Biopsy Device," filed Jun. 1, 2011, published as U.S. Pat. Pub. No. 2012/0310110 on Dec. 6, 2012; U.S. Non-Provisional patent application Ser. No. 13/205,189, entitled "Access Chamber and Markers for Biopsy Device," filed Aug. 8, 2011; U.S. Non-Provisional patent application Ser. No. 13/218,656, entitled "Biopsy Device Tissue Sample Holder with Bulk Chamber and Pathology Chamber," filed Aug. 26, 2011; and U.S. Provisional Patent App. No. 61/727,889, entitled "Biopsy System with Graphical User Interface," filed Nov. 19, 2012. The disclosure of each of the above-cited U.S. patents, U.S. patent application Publications, U.S. Non-Provisional patent applications, and U.S. Provisional patent application is incorporated by reference herein. Of course biopsy device (10) may be constructed in any other manner as will be apparent to one of ordinary skill in the art in view of the teachings herein.

II. Overview of Exemplary Control Unit

Referring back to FIG. 1, control unit (20) of the present example comprises a valve assembly receptacle (22), a pair of valve actuators (24), and a vacuum canister (26). Valve assembly receptacle (22) is configured to receive a proximal end (206) of a valve assembly (200) of valve assembly unit (100), as will be described in greater detail below. Receptacle (22) of the present example includes a substantially rectangular central portion (not shown) having a downward ledge (not shown) that longitudinally secures valve assembly (200) to control unit (20) when valve assembly (200) is inserted therein. In addition, a pair of cylindrical receptacles (not shown) for receptacle (22) are axially aligned with a corresponding valve actuator (24). When valve assembly (200) is inserted into receptacle (22), a shaft of each actuator (24) is keyed to insert into a key slot (228, 328) of a corresponding valve spool (214, 314) of valves (210, 300) such that rotation of one or both shafts of actuators (24) rotate a corresponding valve spool (214, 314). In the present example, actuators (24) comprise stepper motors, though it should be understood that other motors or control devices to rotate valve spools (214, 314) may be used, as will be apparent to one of ordinary skill in the art in view of the teachings herein.

Actuators (24) drive first valve (210) and second valve (300) according to a sequence or sequences to control the flow of fluids through valve assembly (200) during a biopsy procedure. Merely exemplary sequences for controlling biopsy device (10) may be configured such as those disclosed in U.S. Pat. No. 7,938,786, entitled "Vacuum Timing Algorithm for Biopsy Device," issued May 10, 2011; in U.S. Non-Provisional patent application Ser. No. 12/953,715, entitled "Handheld Biopsy Device with Needle Firing," filed Nov. 24, 2010, published as U.S. Pat. Pub. No. 2012/0109007 on May 3, 2012, the disclosures of which are incorporated by reference herein; and/or in any other manner as will be apparent to one of ordinary skill in the art in view of the teachings herein. The sequences of the present example are pre-programmed into the control unit (20) so that either a negative (vacuum) pressure, an ambient (atmospheric) pressure (e.g., venting), a dead head, and/or a saline supply is supplied to the lines (102, 104, 106) to biopsy device (10), as will be described in greater detail below. In some versions, the sequences may be manually controlled via buttons, knobs, touch screen icons, other components associated with control unit (20). In addition, or in the alternative, the sequences may be pre-programmed or controlled by biopsy device (10), such as via onboard circuitry or buttons on biopsy device (10). In yet a further version, the sequences may be controlled by a remote control or by a computer operatively coupled to control unit (20) and/or biopsy device (10). Of course still further configurations will be apparent to one of ordinary skill in the art in view of the teachings herein. Control unit (20) may be further constructed in accordance with at least some of the teachings of U.S. Pat. No. 6,162,187, entitled "Fluid Collection Apparatus for a Surgical Device," issued Dec. 19, 2000, the disclosure of which is incorporated by reference herein; or in accordance with any other manner as will be apparent to one of ordinary skill in the art in view of the teachings herein.

Control unit (20) also includes a vacuum canister (26) through which a vacuum is provided to biopsy device (10). Vacuum canister (26) is configured such that fluids from biopsy device (10) are deposited within vacuum canister (26) while a vacuum is provided to biopsy device. Vacuum canister may be further constructed in accordance with at least some of the teachings of U.S. Pat. No. 7,575,556, entitled "Deployment Device Interface for Biopsy Device," issued Aug. 18, 2009; and/or U.S. Pat. Pub. No. 2008/0146962, entitled "Biopsy System with Vacuum Control Module," published Jun. 19, 2008, the disclosures of which are incorporated by reference herein. While vacuum canister (26) is shown within control unit (20), it should be understood that vacuum canister (26) may be a separate component outside of control unit (20) or, in some versions, a vacuum canister (26) may be integrated into biopsy device (10). Of course further constructions and/or configurations for vacuum canister (26) will be apparent to one of ordinary skill in the art in view of the teachings herein.

III. Exemplary Valve Assembly Unit

Figure 3:
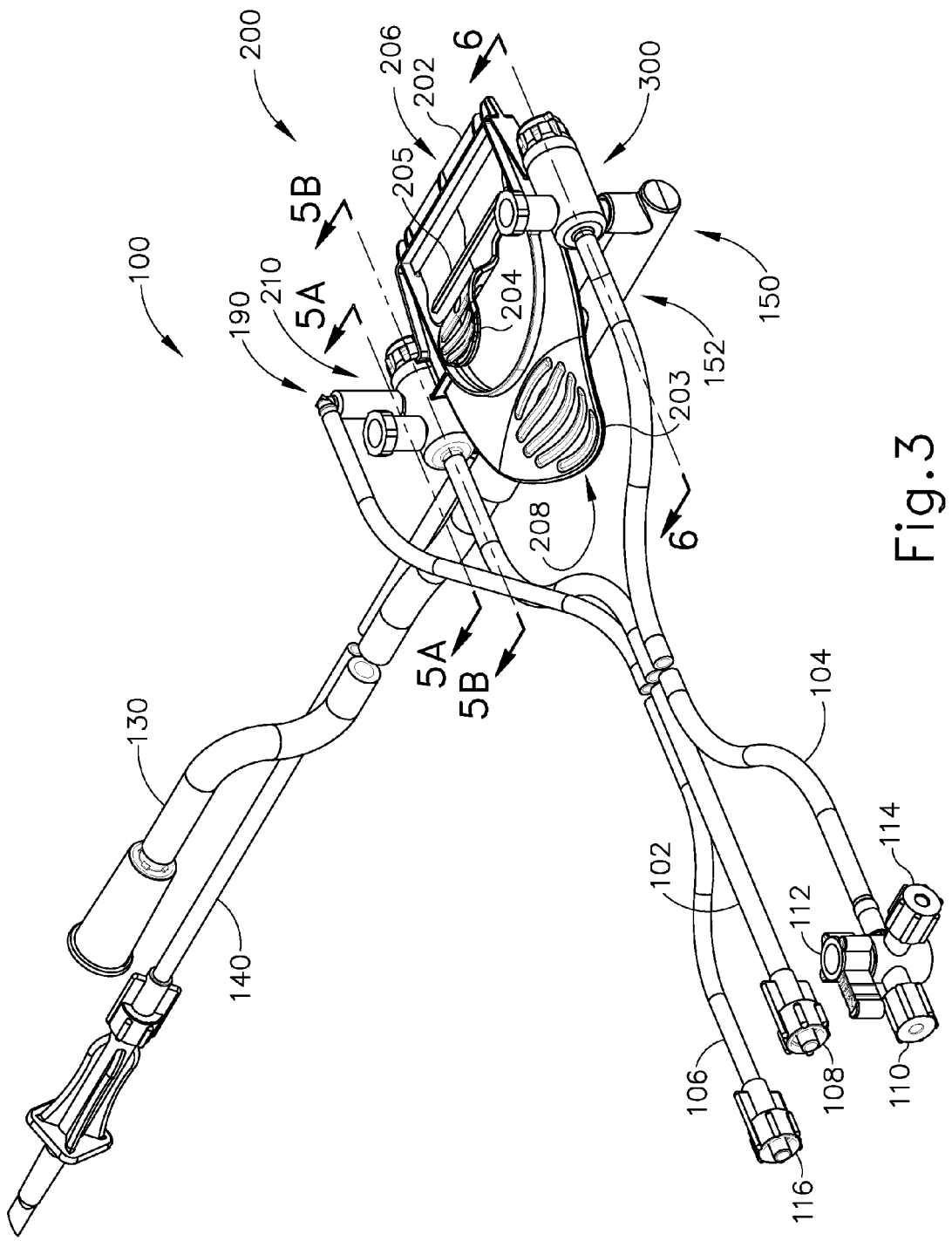
FIG. 3 depicts a perspective view of the valve assembly unit of FIG. 1 showing an exemplary valve assembly and a plurality of tubes.

As shown in FIGS. 1 and 3, valve assembly unit (100) comprises a valve assembly (200) and a plurality of tubes (102, 104, 106, 130, 140) in fluid communication with valve assembly (200). Tubes (102, 104, 106, 130, 140) may come pre-assembled with valve assembly (200) or may be assembled by a user with valve assembly (200) separately. Biopsy device (10) is fluidly coupled to valve assembly (200) via a plurality of tubes (102, 104, 106). In the present example, three tubes (102, 104, 106) fluidly couple biopsy device (10) to valve assembly (200). Of course it should be understood that two tubes, one tube, or more than three tubes may be used to fluidly couple biopsy device (10) to valve assembly (200). In the present example, tubes (102, 104, 106) comprise a first tube (102), a second tube (104), and a third tube (106). As shown in FIG. 3, tubes (102, 104, 106) terminate with a corresponding luer connector (108, 110, 116) to selectively couple and decouple tubes (102, 104, 106) from biopsy device (10) and/or other tubes. In the present example, first tube (102) fluidly couples first valve (210) to biopsy device (10) to provide a negative lateral (vacuum) pressure. By way of example only, a connector coupled to biopsy device (10) may be in fluid communication with second lumen (38) of needle (16) and configured to couple to first tube (102) such that first tube (102) is fluidly coupled to needle (16) to provide lateral vacuum to second lumen (38). The lateral vacuum is thereby communicated to lateral aperture (34) in needle (16) through openings (37). Second tube (104) fluidly couples second valve (300) to biopsy device (10) to provide a negative axial (vacuum) pressure. By way of example only, a connector coupled to biopsy device (10) may be in fluid communication with cutter lumen (52) of needle (16) and configured to couple to second tube (104) such that second tube (104) is fluidly coupled to needle (16) to provide an axial vacuum through cutter lumen (52). Third tube (106) fluidly couples a saline connector (190) to biopsy device (10) such that a source of saline may be selectively provided to biopsy device (10). By way of example only, a connector coupled to biopsy device (10) may be in fluid communication with second lumen (38) and/or other portions of needle (16) and configured to couple to third tube (106) such that third tube (106) is fluidly coupled to needle (16) to provide saline to needle (16). Of course it should be understood that tubes (102, 104, 106) may be coupled to biopsy device (10) and/or valve assembly (200) in other manners and/or for other purposes, as will be apparent to one of ordinary skill in the art in view of the teachings herein.

In the present example, second tube (104) includes a T-valve (112) between second tube (104) and luer connector (110). T-valve (112) includes a luer connector (114) that may be selectively fluidly coupled to another fluid source or other item. By way of example only, luer connector (114) may be coupled to a source of medicaments, such as Lidocaine, for use during a biopsy procedure. T-valve (112) is used to switch luer connector (110) from being fluidly coupled to second tube (104) and the source of medicaments though this is merely optional. Still further configurations for tubes (102, 104, 106), luer connectors (108, 110, 114, 116), and/or T-valve (112) will be apparent to one of ordinary skill in the art in view of the teachings herein.

Figure 4:
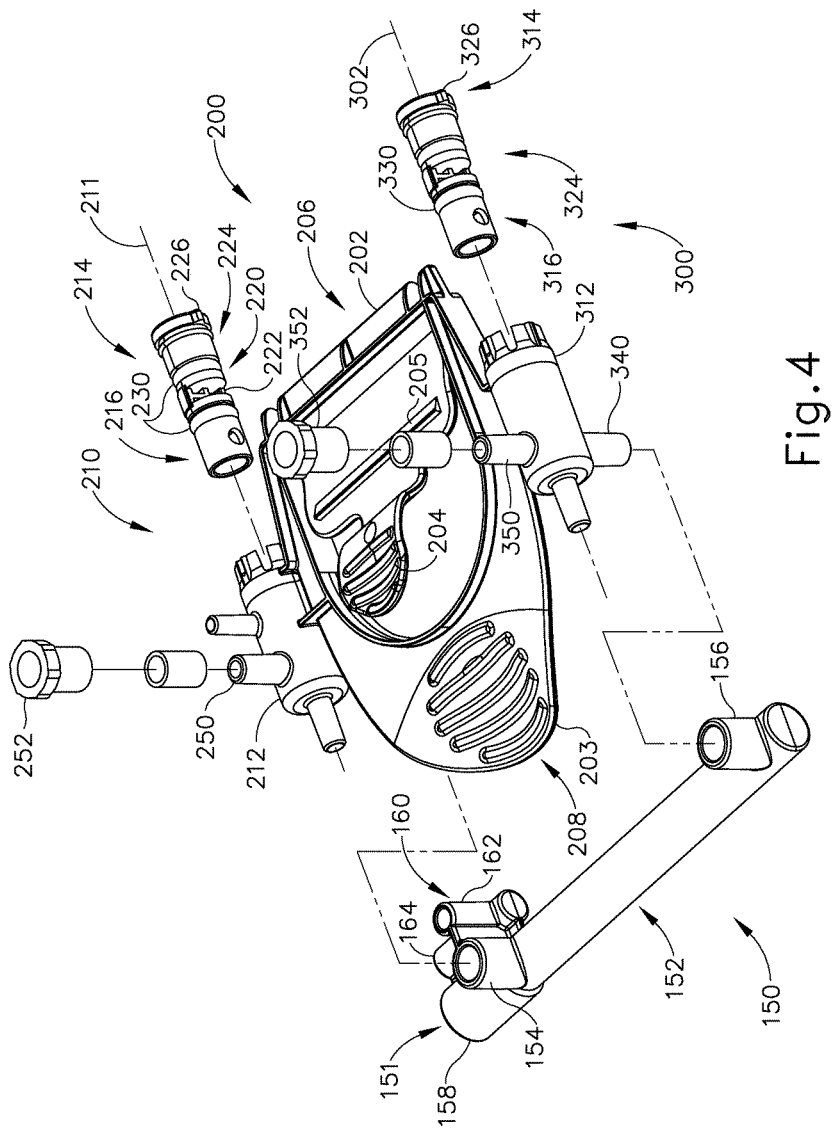
FIG. 4 depicts an exploded perspective view of the valve assembly of FIG. 3.
Figure 5A:
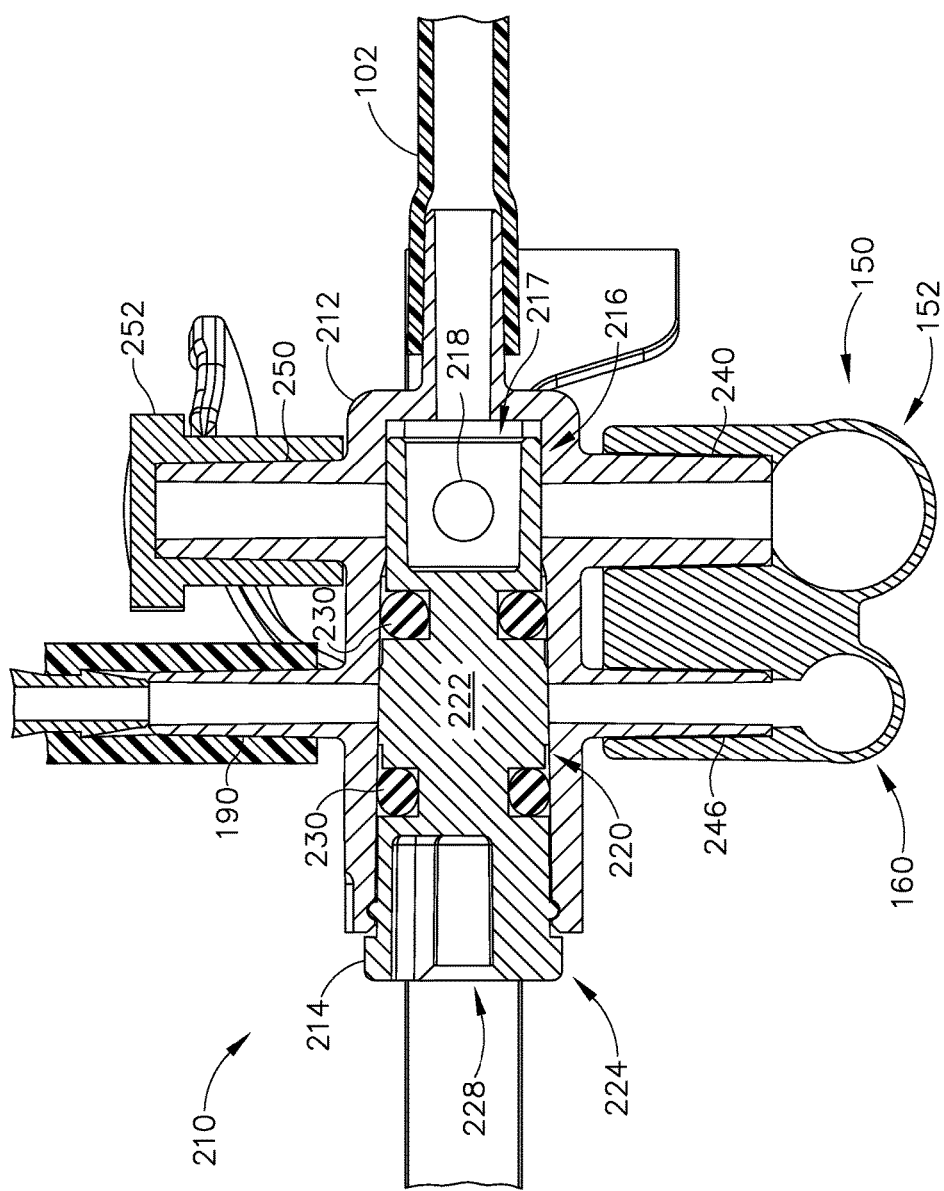
FIG. 5A depicts a cross-sectional view of a first valve of the valve assembly of FIG. 3 taken along section line 5A-5A shown in FIG. 3 showing an exemplary first valve spool in a first position.
Figure 6A:
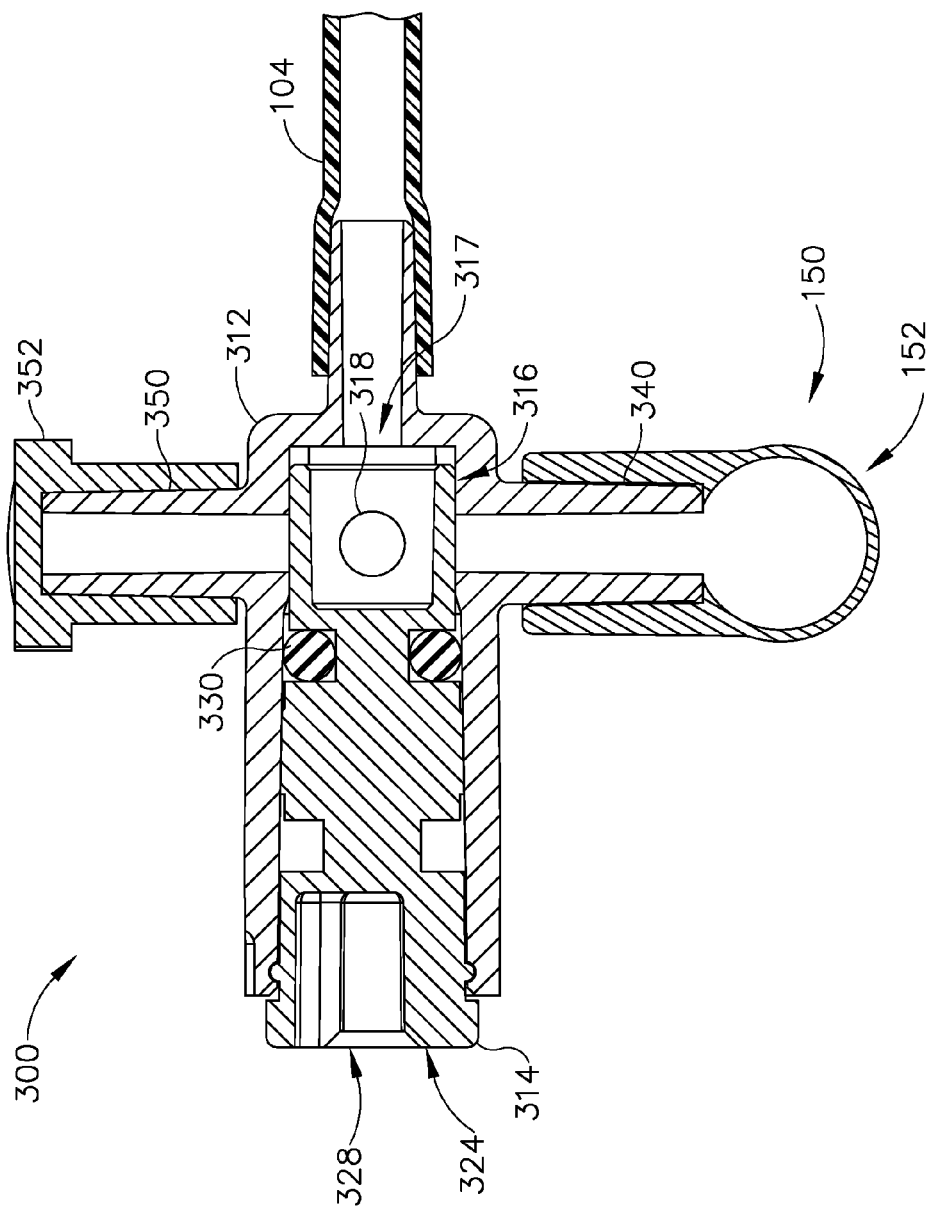
FIG. 6A depicts a cross-sectional view of a second valve of the valve assembly of FIG. 3 taken along section line 6-6 shown in FIG. 3 showing an exemplary second valve spool in a first position.

In addition to tubes (102, 104, 106) fluidly coupling valve assembly (200) to biopsy device (10), tubes (130, 140)

fluidly couple valve assembly (200) to vacuum canister (26) and saline bag (50), shown in FIG. 1. Fourth tube (130) is in fluid communication with vacuum canister (26). Fifth tube (140) is in fluid communication with saline bag (50). In the present example, fourth tube (130) and fifth tube (140) are joined to and in fluid communication with tubular member (150), though it should be noted that fourth tube (130) and fifth tube (140) are not in fluid communication with each other. Tubular member (150) comprises a longitudinal portion (152) and an L-shaped portion (160). As shown best in FIG. 4, longitudinal portion (152) and L-shaped portion (160) are merely physically joined together to form tubular member (150) and are not in fluid communication. As shown in FIGS. 4, 5A, and 6A, longitudinal portion (152) comprises a longitudinal tube having a pair of transverse connectors (154, 156) configured to fluidly couple fourth tube (130) with a first connector (240) of first valve (210) and a connector (340) of second valve (300) of valve assembly (200), respectively. A longitudinal connector (158) at a first end (151) of tubular member (150) fluidly couples to and secures fourth tube (130) to tubular member (150). L-shaped portion (160) comprises a transverse connector (162) and a longitudinal connector (164). Transverse connector (162) fluidly couples to a second connector (246) of first valve (210), as shown best in FIG. 5A. Longitudinal connector (164) extends from first end (151) of tubular member (150) and fluidly couples to and secures fifth tube (140) to tubular member (150). Of course it should be understood that L-shaped portion (160) and longitudinal portion (152) may be separate discrete pieces. Further configurations for tubular member (150) will be apparent to one of ordinary skill in the art in view of the teachings herein.

Valve assembly (200) of the present example comprises a first valve (210) having a first axis (211), a second valve (300) having a second axis (302), which is parallel to first axis (211), shown in FIG. 4. First valve (210) and second valve (300) are affixed in parallel alignment onto a valve frame (202). Valve frame (202) comprises a valve frame handle (203), a latch lever (204), a proximal end (206), and a distal end (208). In the present example, latch lever (204) is cantileverly attached to valve frame (202) and is disposed between first valve (210) and second valve (300). Latch lever (204) includes a latching feature (205) and is resiliently biased such that when valve assembly (200) is inserted into receptacle (22) of control unit (20), latching feature (205) selectively secures valve assembly (200) to receptacle (22), as noted above. Of course is should be understood that other securing features may be used to selectively couple valve assembly (200) to control unit (20), such as adhesives, screws, bolts, clips, clamps, hook and loop connectors, etc.

A. Exemplary First Valve

First valve (210) comprises a first valve spool (214) rotatably inserted into a first valve housing (212). As shown in FIGS. 5A-5D, first valve spool (214) comprises a cylindrical member having a first valve portion (216), a second valve portion (220), a proximal end (224), and a key slot (228) located within proximal end (224) of first valve spool (214). A pair of o-rings (230) are located between first valve portion (216) and second valve portion (220) and between second valve portion (220) and proximal end (224). In the present example, o-rings (230) substantially seal each valve portion (216, 220) within valve housing (212) and also fluidly isolates each valve portion (216, 220) from the other valve portion (216, 220). It should be understood that the distal end of valve housing (212) is fluidly coupled and sealed to first tube (102) such that first valve portion (216) is fluidly sealed by o-ring (230) when first valve spool (214) is inserted into first valve housing (212). First valve spool (214) further includes an indicator (226), shown in FIG. 4, extending radially outward at the proximal end of first valve spool (214) and indicates the orientation of hole (218), described in greater detail below. It should be understood that indicator (226) is merely optional and may be omitted. First valve housing (212) comprises a hollow cylindrical member that is coupled to and in fluid communication with a first connector (240), a second connector (246), a first vent connector (250), and saline connector (190). In the present example, second connector (246) and saline connector (190) lie in a plane that is offset, but parallel to a vertical plane containing first axis (211). Accordingly, a hemi-cylindrical portion (222) of first valve spool (214) may selectively block both second connector (246) and saline connector (190) or may permit fluid communication between both second connector (246) and saline connector (190), as will be described in more detail below. A first vent (252) is fluidly coupled to first vent connector (250). First vent (252) of the present example includes a semi-permeable filter mesh capable of allowing atmospheric air into and out of first vent connector (250).

In the present example, first valve portion (216) comprises a hollow cylindrical member having an open distal end (217) and a transverse hole (218). Hole (218) is configured to selectively align with first connector (240) of first valve housing (212), with first vent connector (250), and/or to substantially fluidly isolate the interior of first valve portion (216) depending upon the orientation of first valve spool (214). Accordingly, when an actuator (24) is coupled to key slot (228), actuator (24) is able to control the orientation of hole (218) relative to first connector (240), first vent connector (250), and/or otherwise. Thus, actuator (24) is operable to control whether first valve (210) vents first tube (102) to atmosphere via first vent (252) or supplies vacuum to first tube (102) via tubular member (150) and fourth tube (130).

Second valve portion (220) comprises an axial hemi-cylindrical portion (222), shown best in FIG. 4, such that an opposing hemi-cylindrical space is formed within first valve housing (212). In this configuration, hemi-cylindrical portion (222) is configured to selectively align such that second connector (246) and saline connector (190) are in fluid communication, or to substantially fluidly isolate second connector (246) relative to saline connector (190) depending upon the orientation of first valve spool (214). Accordingly, when an actuator (24) is coupled to key slot (228), actuator (24) is able to control the orientation of hemi-cylindrical portion (222) relative to second connector (246) and saline connector (190). Thus, actuator (24) is operable to control whether first valve (210) fluidly couples fifth tube (140) to saline connector (190) that is in fluid communication with third tube (106) and saline bag (50). Of course further configurations for first valve (210) will be apparent to one of ordinary skill in the art in view of the teachings herein.

B. Exemplary Second Valve

Figure 6B:
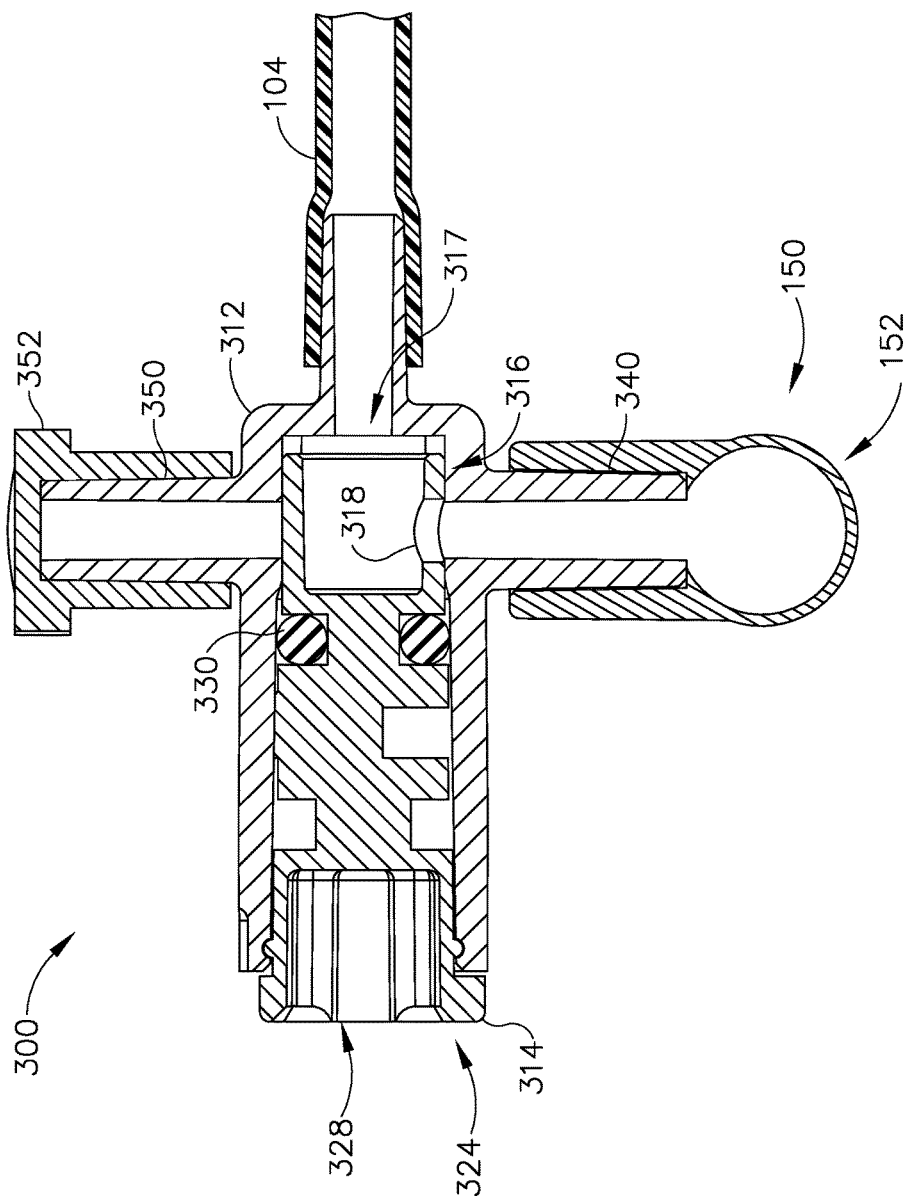
FIG. 6B depicts a cross-sectional view of the second valve of FIG. 3 taken along section line 6-6 shown in FIG. 3 showing the second valve spool in a second position.
Figure 6C:
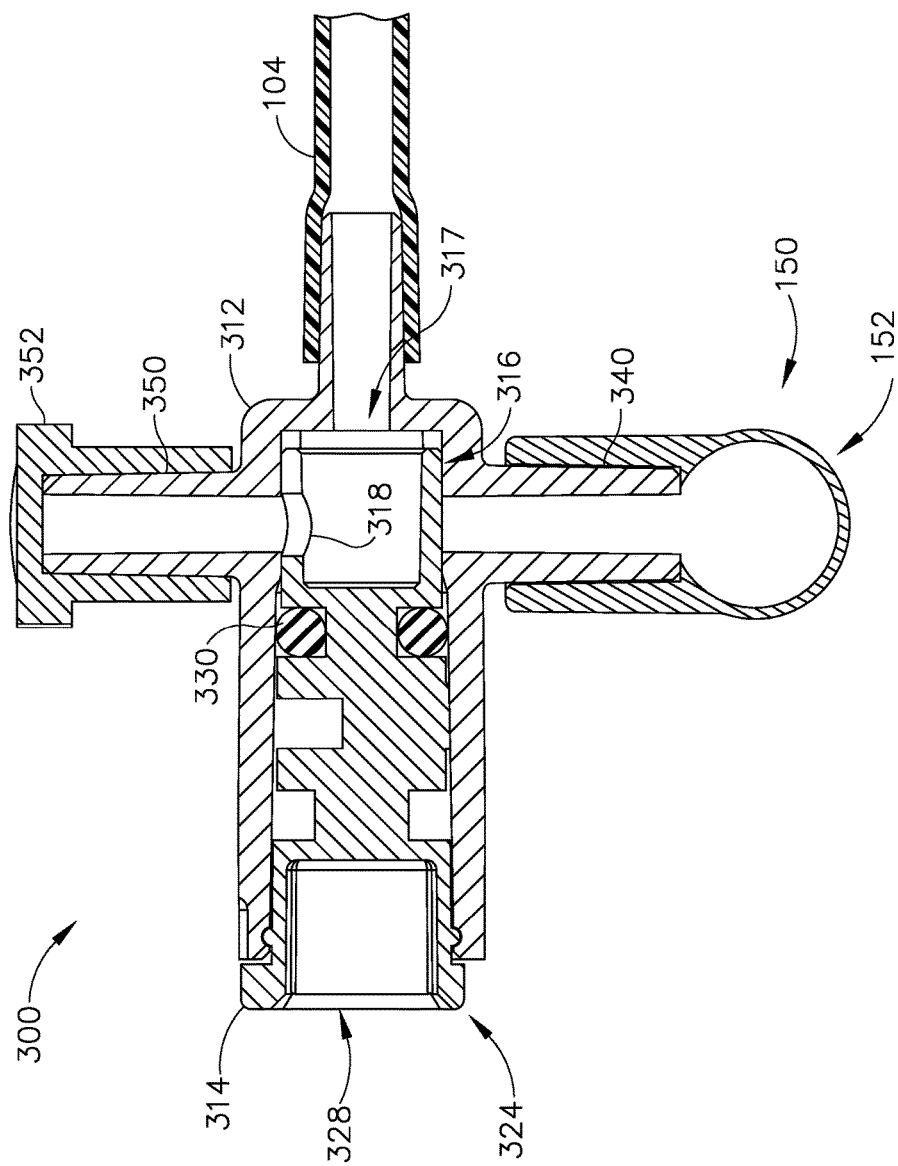
FIG. 6C depicts a cross-sectional view of the second valve of FIG. 3 taken along section line 6-6 shown in FIG. 3 showing the second valve spool in a third position.

Second valve (300) comprises a second valve spool (314) rotatably inserted into a first valve housing (312). As shown in FIGS. 6A-6C, second valve spool (314) comprises a cylindrical member having a first valve portion (316), a proximal end (324), and a key slot (328) located within proximal end (324) of second valve spool (314). An o-ring (330) is located between first valve portion (316) and proximal end (324). In the present example, o-ring (330) substantially seals first valve portion (316) within valve housing (312) and also fluidly isolates first valve portion (316) from proximal end (324). It should be understood that the distal end of valve housing (312) is fluidly coupled and sealed to second tube (104) such that first valve portion (316) is fluidly sealed by o-ring (330) when second valve spool (314) is inserted into second valve housing (312). Second valve spool (314) further includes an indicator (326) extending radially outward at the proximal end of second valve spool (314) and indicates the orientation of hole (318), described in greater detail below. It should be understood that indicator (326) is merely optional and may be omitted. Second valve housing (312) comprises a hollow cylindrical member that is coupled to and in fluid communication with a connector (340) and a second vent connector (350). A second vent (352) is fluidly coupled to second vent connector (350). Second vent (352) includes a semi-permeable filter mesh capable of allowing atmospheric air into and out of second vent connector (350).

In the present example, first valve portion (316) comprises a hollow cylindrical member having an open distal end (317) and a transverse hole (318). Hole (318) is configured to selectively align with connector (340) of second valve housing (312), with second vent connector (350), and/or to substantially fluidly isolate the interior of first valve portion (316) depending upon the orientation of second valve spool (314). Accordingly, when an actuator (24) is coupled to key slot (328), actuator (24) is able to control the orientation of hole (318) relative to connector (340), second vent connector (350), and/or otherwise. Thus, actuator (24) is operable to control whether second valve (300) vents second tube (104) to atmosphere via second vent (352) or supplies vacuum to second tube (104) via tubular member (150) and fourth tube (130).

In the present example, valve frame (202), first valve (210), second valve (300), latch lever (204), and valve handle (203) may be made from a medical grade, rigid, injection molded plastic such as polycarbonate. All of the fluid carrying tubes described for valve assembly (200) (including first tube (102), second tube (104), third tube (106), fourth tube (130), and/or fifth tube (150)) may be made of an economical, flexible, medical grade material such as polyvinyl chloride (PVC). First valve spool (214) and second valve spool (314) are preferably made from a rigid, medical grade plastic such as polyethylene.

In the present example, when valve assembly (200) is to be correctly inserted into valve assembly receptacle (22) such that actuators (24) align with and couple to valve spools (214, 314), first axis (202) is aligned with the first cylindrical receptacle and second axis (302) is aligned with the second cylindrical receptacle, as described above. While first valve (210) and second valve (300) are described as rotary valves, other types of valves may be used as will be apparent to one of ordinary skill in the art in view of the teachings herein.

C. Exemplary Operational States of First Valve and Second Valve

Figure 7:
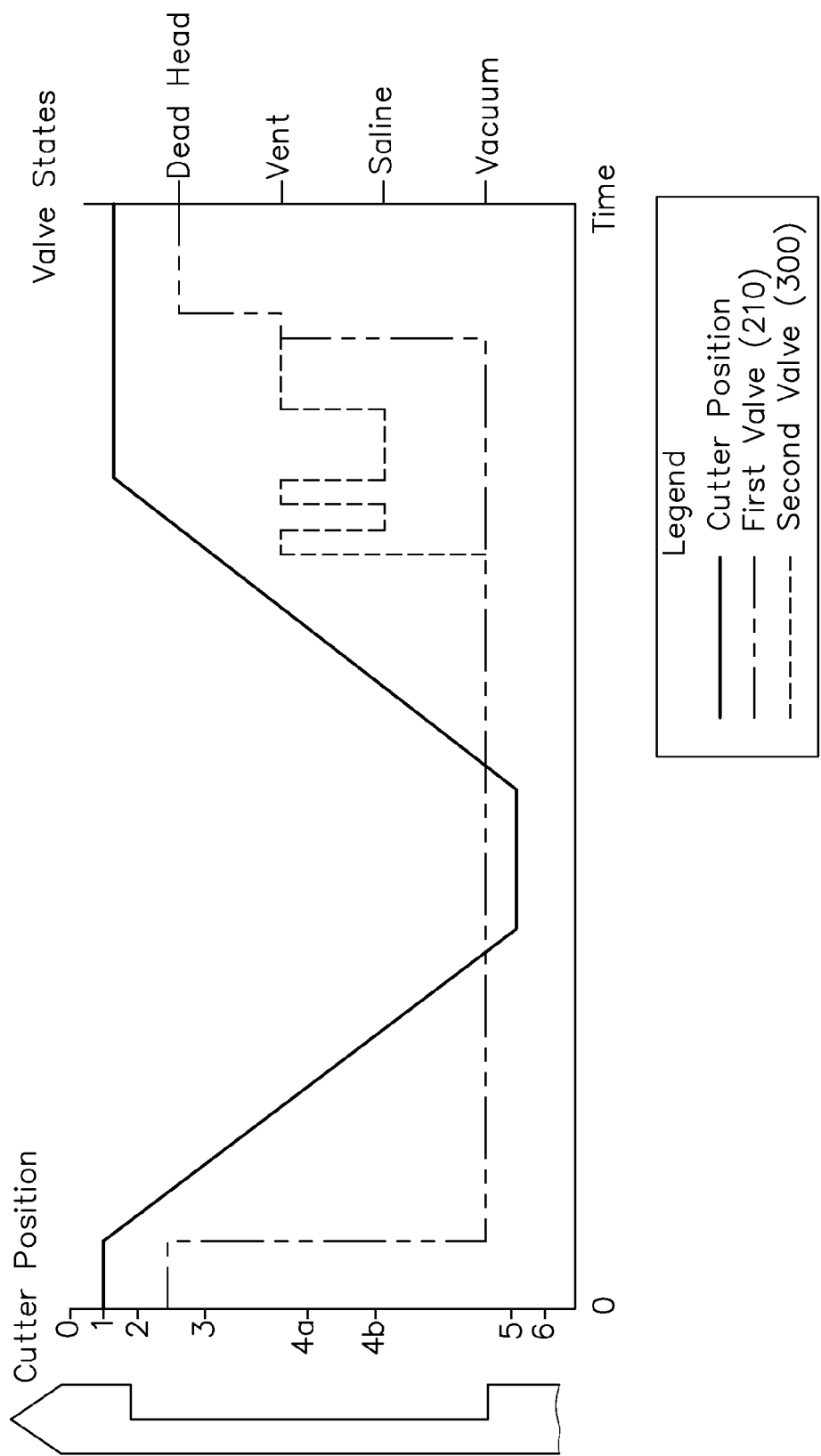
FIG. 7 depicts a graph view of an exemplary operational process showing exemplary states of the first valve and second valve relative to time and a cutter position.

As shown in FIGS. 5A-6C, first valve (210) and second valve (300) are controlled via actuators (24) for different operational states. FIG. 7 depicts an exemplary operational process showing the states of first valve (210) and second valve (300) relative to the position of cutter (50) and time. This operational process may constitute a single cutting stroke of cutter (50) to acquire a single tissue sample, and may be repeated as many times as desired to obtain as many tissue samples as desired. In a first state, both first valve (210) and second valve (300) are in a "dead head" or sealed state such that no fluid is provided through tubes (102, 104, 106). In this state, first valve spool (214) is rotated such that hole (218) is not aligned with either first connector (240) or first vent connector (250), as shown in FIG. 5A, such that first tube (102) is not in fluid communication with either vent (252) or fourth tube (130). In addition, first valve spool (214) is oriented such that hemi-cylindrical section (222) substantially blocks fluid transfer from second connector (246) to saline connector (190) such that saline from saline bag (50) is not delivered to third tube (106). It should be understood that the cross-sectional view shown in FIG. 5A is set off from axis (202) to show connectors (190, 246) that are axially offset, as noted above. In this first state, second valve spool (314) is rotated such that hole (318) is not aligned with either connector (340) or second vent connector (350), as shown in FIG. 6A, such that second tube (104) is not in fluid communication with either vent (352) or fourth tube (130). Thus, valve assembly unit (100) provides substantially no fluids to biopsy device (10). As shown in FIG. 7, initially both valves (210, 300) begin in this state with cutter (50) advanced to position 1 such that lateral aperture (34) of needle (16) is closed.

Figure 5B:
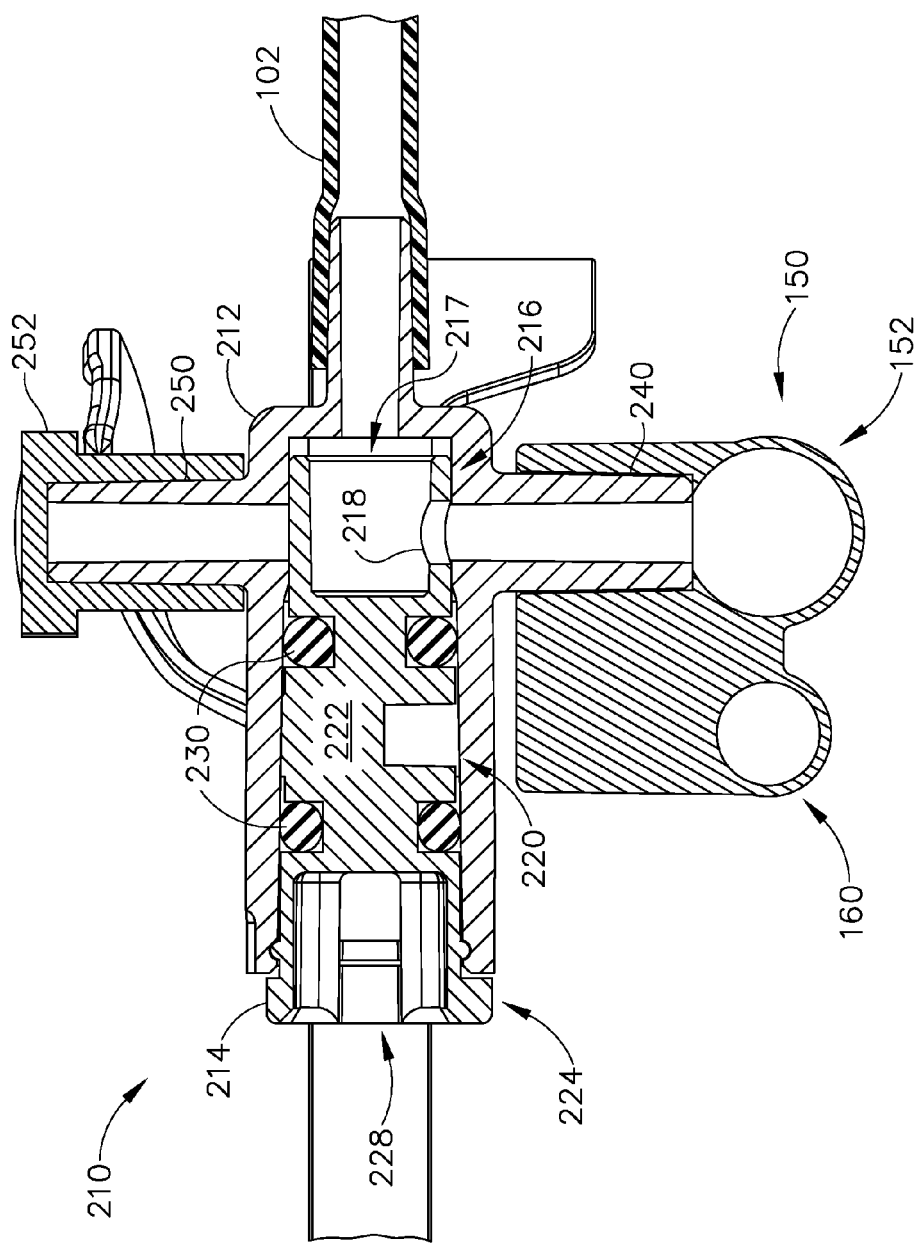
FIG. 5B depicts a cross-sectional view of the first valve of FIG. 3 taken along section line 5B-5B shown in FIG. 3 showing the first valve spool in a second position.

In a second state, both first valve (210) and second valve (300) are in a vacuum state such that a negative (vacuum) pressure is provided through first tube (102) and second tube (104). In this state, first valve spool (214) is rotated by a corresponding actuator (24) such that hole (218) is aligned with first connector (240) of first valve housing (212), as shown in FIG. 5B. Accordingly, vacuum from fourth tube (130) is in fluid communication with first tube (102) such that a lateral vacuum is supplied to second lumen (38) of biopsy device (10). It should be understood that in this orientation, hemi-cylindrical portion (222) of first valve spool (214) is positioned such that saline connector (190) is not in fluid communication with second connector (246) of first valve housing (212). Accordingly, saline from saline bag (50) and fifth tube (140) is not in fluid communication with third tube (106). Also in this state, second valve spool (314) is rotated by a corresponding actuator (24) such that hole (318) is aligned with connector (340) of second valve housing (312), as shown in FIG. 6B. Accordingly, vacuum from fourth tube (130) is also in fluid communication with second tube (104) such that an axial vacuum is supplied to cutter lumen (52) of biopsy device (10). As shown in FIG. 7, both valves (210, 300) are rotated into this state as cutter (50) is retracted to open lateral aperture (34) of needle (16). Both valves (210, 300) remain in this state such that tissue may be drawn into lateral aperture (34) of needle (16) of biopsy device (10) after cutter (50) is retracted and for a predetermined period as cutter (50) is advanced to sever the tissue.

Figure 5C:
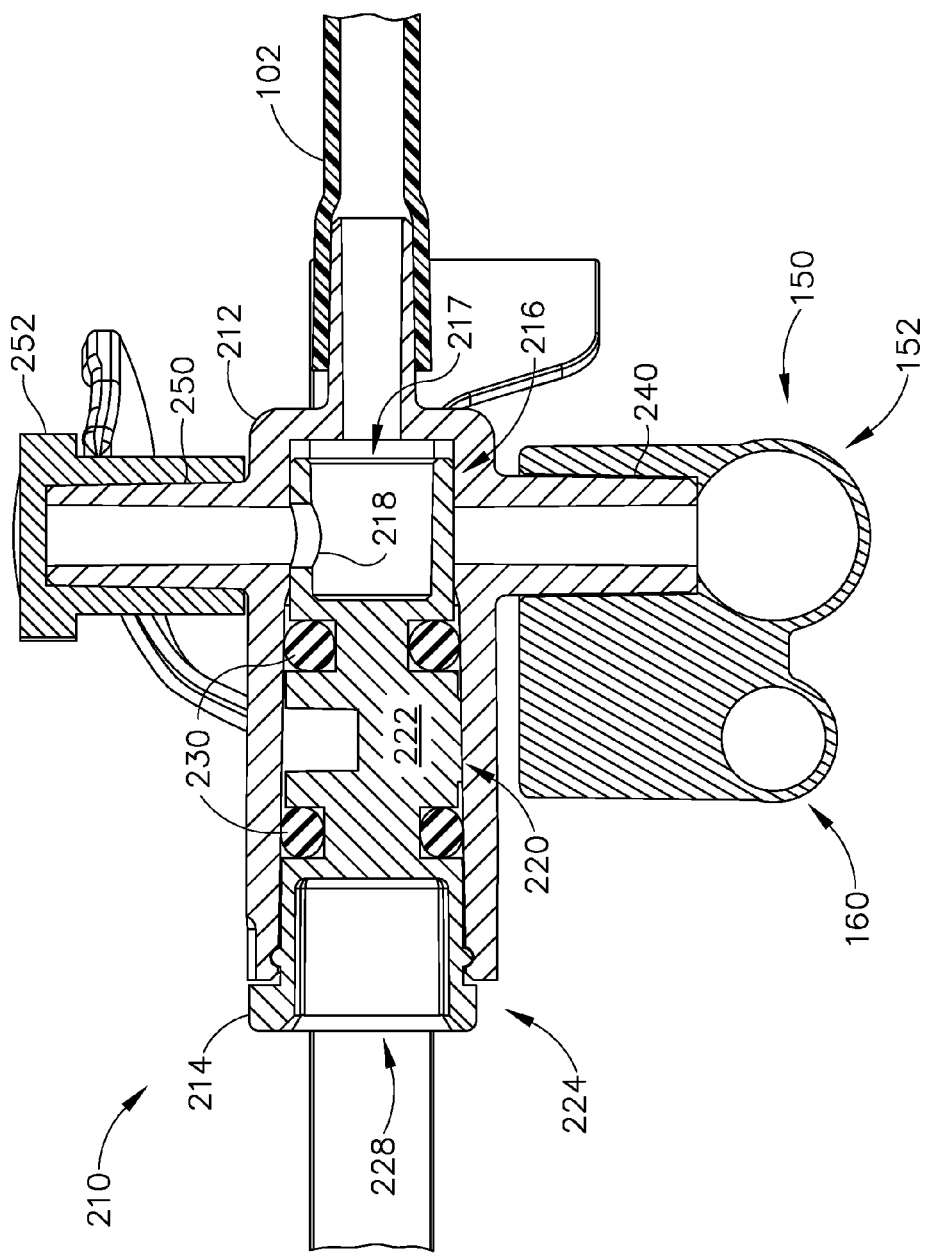
FIG. 5C depicts a cross-sectional view of the first valve of FIG. 3 taken along section line 5B-5B shown in FIG. 3 showing the first valve spool in a third position.

In a third state, first valve (210) is rotated to a vent position such that an atmospheric pressure is provided through first tube (102) while second valve (300) remains in a vacuum state such that a negative (vacuum) pressure is provided second tube (104). In this state, first valve spool (214) is rotated by a corresponding actuator (24) such that hole (218) is aligned with first vent connector (250) such that first tube (102) is in fluid communication with first vent (252), as shown in FIG. 5C. It should be understood that in this orientation, hemi-cylindrical member (222) of first valve spool (214) is positioned such that saline connector (190) is not in fluid communication with second connector (246) of first valve housing (212). Accordingly, saline from saline bag (50) and fifth tube (140) is not in fluid communication with third tube (106). In this third state, second valve spool (314) remains in the position shown in FIG. 6B and described above such that an axial vacuum is provided through second tube (104). In this state, the severed tissue sample may continue to be drawn axially through biopsy device (10) towards tissue sample holder (18) or, in some versions, any tissue debris within needle (16) is cleared from therein via the axial vacuum.

Figure 5D:
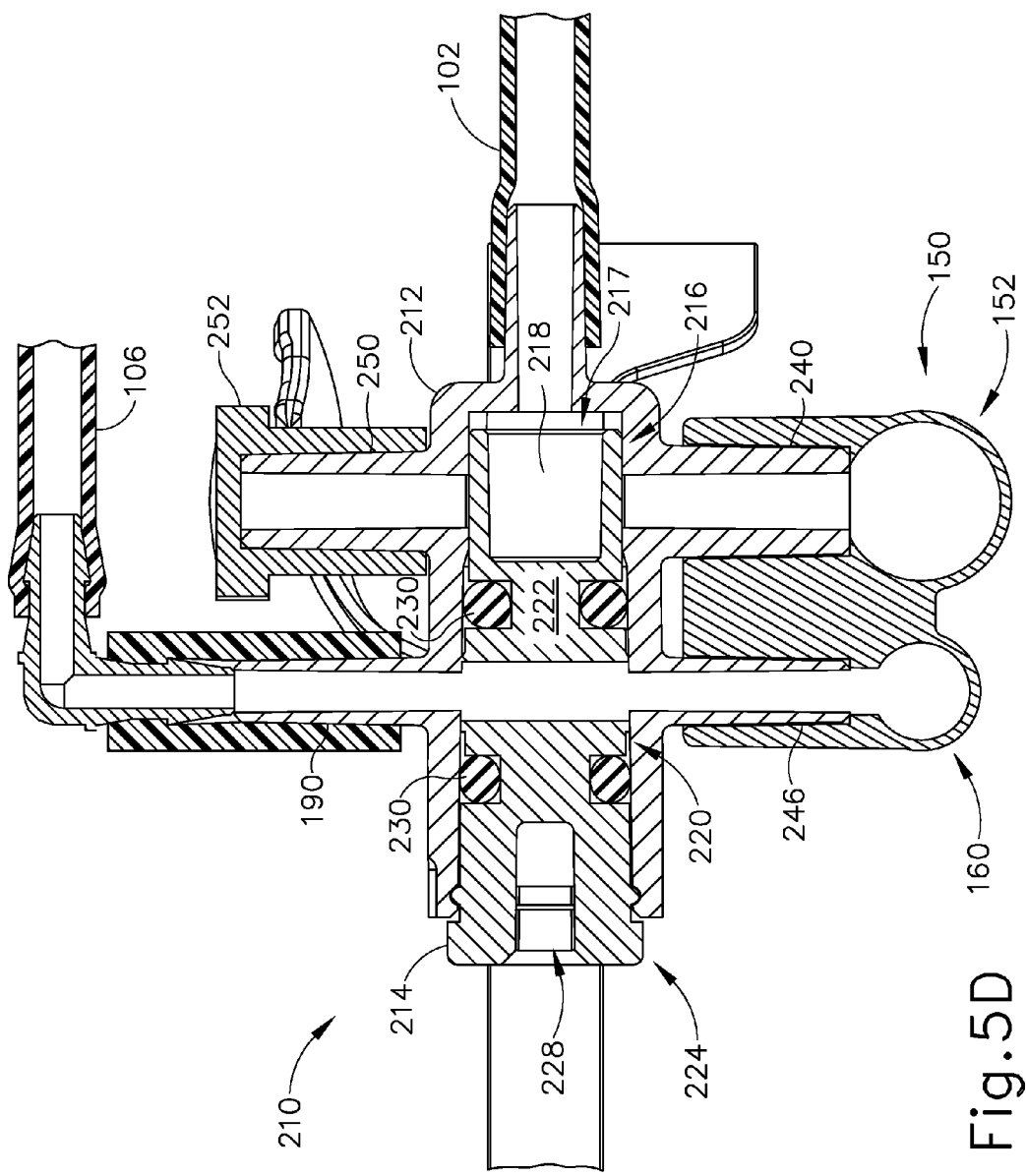
FIG. 5D depicts a cross-sectional view of the first valve of FIG. 3 taken along section line 5A-5A shown in FIG. 3 showing the first valve spool in a fourth position.

In a fourth state, first valve (210) is rotated to a saline position such that saline is provided from saline bag (50) through first tube (102) while second valve (300) remains in a vacuum state such that a negative (vacuum) pressure is provided second tube (104). In this state, first valve spool (214) is rotated by a corresponding actuator (24) such that hemi-cylindrical portion (222) does not impede fluid flow from saline connector (190) to second connector (246) of first valve housing (212), as shown in FIG. 5D. Accordingly, saline from saline bag (50) and fifth tube (140) is in fluid communication biopsy device (10) via third tube (106). It should be understood that in this orientation, hole (218) of first valve spool (214) is positioned such that neither first connector (240) nor first vent connector (250) is in fluid communication with first tube (102). In this state, second valve spool (314) remains in the position shown in FIG. 6B and described above such that an axial vacuum is provided through second tube (104). Accordingly, the axial vacuum provided by second tube (104) is used in biopsy device (10) to draw saline through third tube (106) and to draw a severed tissue sample axially through biopsy device (10) towards tissue sample holder (18). In some versions this state may occur when cutter (50) of biopsy device (10) is between 70% closed, inclusive, and fully closed, inclusive. Of course this state may occur at other positions of cutter (50), as will be apparent to one of ordinary skill in the art in view of the teachings herein. As shown in FIG. 7, first valve spool (214) may be rotated between the third state that vents to atmosphere and the fourth state that provides saline to alternate the supply of atmospheric air and saline to second lumen (38) of needle (16) of biopsy device (10). The alternation of saline and atmospheric air may be used to help flush a severed tissue sample into tissue sample holder (18) and/or clear biopsy device (10) of debris. In the operational process shown in FIG. 7, first valve (210) is rotated to the saline position once cutter (50) is fully closed for a predetermined period of time and then is rotated back to the vent position described above.

In a fifth state, first valve (210) is rotated to a vent position while second valve (300) is rotated to a vent position such that atmospheric pressure is provided to both first tube (102) and second tube (104). In this state, first valve spool (214) is rotated to the position shown in FIG. 5D and described above. Second valve spool (314) is rotated by a corresponding actuator (24) such that hole (318) is aligned with second vent connector (350) of second valve housing (312) such that second tube (104) is in fluid communication with second vent (352), as shown in FIG. 6C. In this state, biopsy device (10) and tubes (102, 104) are vented to atmosphere to remove residual pressure therein. In some versions, first valve (210) and second valve (300) may be rotated back to the first state, the "dead head" state, described above, prior to a new biopsy procedure. For example, as shown in FIG. 7, both first valve (210) and second valve (300) are rotated to the vent positions to relieve residual pressure followed by rotating to the "dead head" state.

In an optional sixth state, first valve (210) may be rotated to a saline position while second valve (300) is rotated to a vent position such that an atmospheric pressure is provided through second tube (104). In this state, first valve spool (214) remains in the saline state described above and shown in FIG. 5C. Second valve spool (314) is rotated to the vent position as shown and described in reference to FIG. 6C. Accordingly, saline is provided to biopsy device (10) without providing axial vacuum. In some versions, T-valve (112) may be operated to provide medicaments from a source coupled to luer connector (114) while second tube (104) is vented. Of course such a state is merely optional.

In some instances, it may be desirable to insert a marker at a biopsy site with biopsy device (10) to provide a visual indication where the tissue sample was taken. For example, a marker applier may be inserted through cutter lumen (52) of cutter (50) to position the marker applier adjacent to lateral aperture (34) within needle (16). With cutter (50) in a retracted position, the user may expel a marker from the marker applier and through lateral aperture (34) of needle (16) for deployment at the biopsy site. The marker may be later visible (or may carry something that is later visible) under some sort of imaging modality (e.g., X-ray, ultrasound, MRI, PEM, BSGI, etc.), enabling a physician to later relocate the biopsy site. By way of example only, the marker and/or marker applier may be constructed in accordance with at least some of the teachings of U.S. application Ser. No. 13/205,189, entitled "Access Chamber and Markers for Biopsy Device," filed on Aug. 8, 2011, the disclosure of which is incorporated by reference herein; and/or U.S. Application Ser. No. 61/727,889, entitled "Biopsy System with Graphical User Interface," filed on Nov. 19, 2012, the disclosures of which are incorporated by reference herein.

The marker applier may be inserted through cutter lumen (52) in at least two different ways. In one example, tissue sample holder (18) remains coupled with probe (12) when the marker applier is inserted. For instance, tissue sample holder (18) may comprise multiple chambers for receiving tissue samples severed by cutter (50) and may have a dedicated chamber to receive a marker applier. The dedicated chamber of tissue sample holder (18) may be aligned with cutter (50) such that the marker applier may be inserted distally through the dedicated chamber of tissue sample holder (18) and through cutter lumen (52) of cutter (50). In another example, the user may first remove tissue sample holder (18) from probe (12), then insert the marker applier through the proximal end of cutter (50) until the marker applier reaches the longitudinal position associated with lateral aperture (34). A new pneumatic state may be activated when the dedicated chamber of tissue sample holder (18) is indexed to cutter lumen (52) and/or or when tissue sample holder (18) is removed from probe (12) to deploy a marker at the biopsy site.

Figure 8:
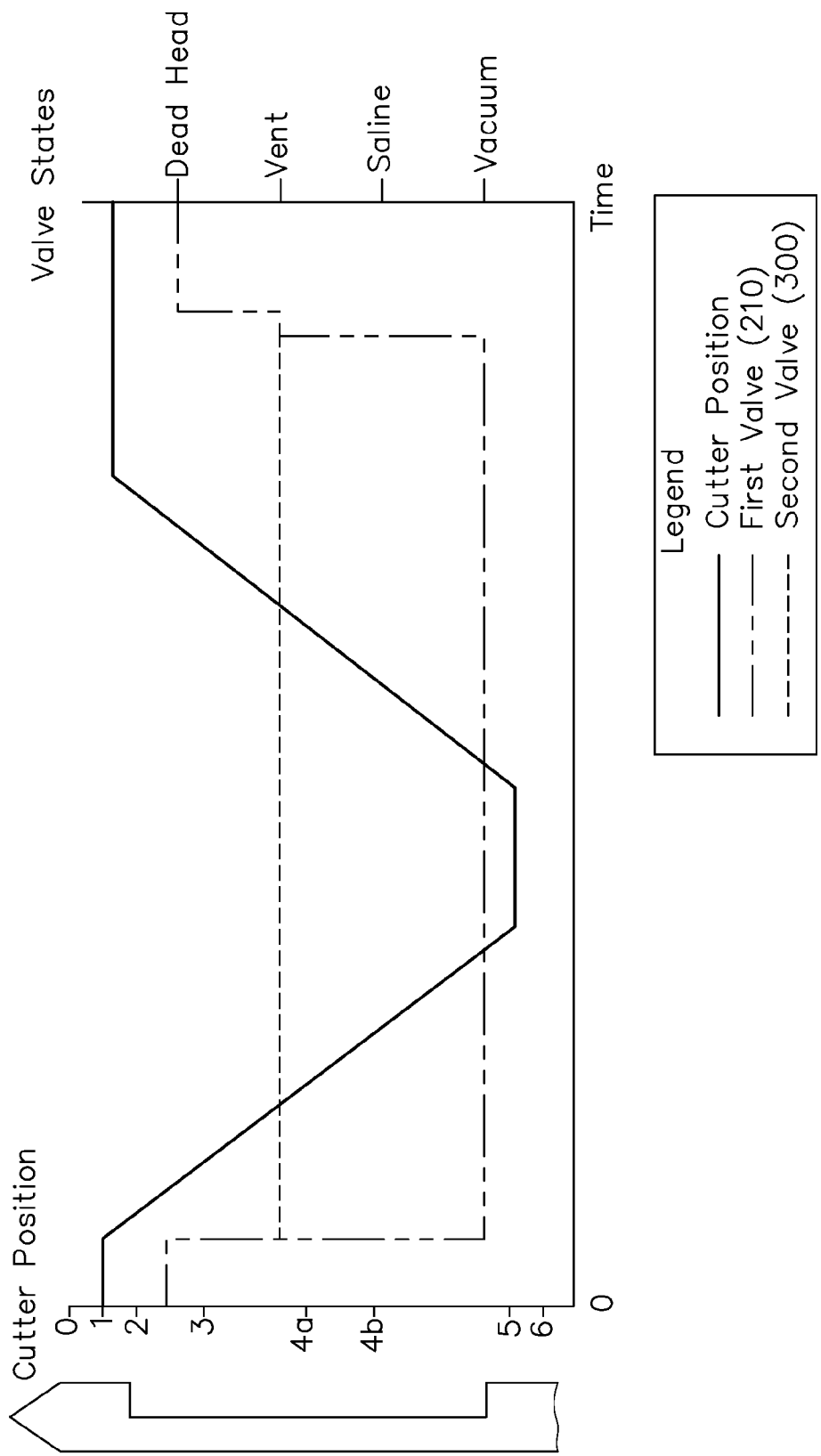
FIG. 8 depicts a graph view of another exemplary operational process showing exemplary states of the first valve and second valve relative to time and a cutter position.

Before the marker is applied, valve assembly (200) may be actuated in accordance with FIG. 8, showing an exemplary operational process of the states of first valve (210) and second valve (300) relative to cutter (50) position and time. In a seventh state, both first valve (210) and second valve (300) are in a "dead head" after a tissue sample has been taken with biopsy device (10). In this state, first valve spool (214) is rotated such that hole (218) is not aligned with either first connector (240) or first vent connector (250), as shown in FIG. 5A, such that first tube (102) is not in fluid communication with either vent (252) or fourth tube (130). In addition, first valve spool (214) is oriented such that hemi-cylindrical section (222) substantially blocks fluid transfer from second connector (246) to saline connector (190) such that saline from saline bag (50) is not delivered to third tube (106). In this seventh state, second valve spool (314) is rotated such that hole (318) is not aligned with either connector (340) or second vent connector (350), as shown in FIG. 6A, such that second tube (104) is not in fluid communication with either vent (352) or fourth tube (130). Thus, valve assembly unit (100) provides substantially no fluids to biopsy device (10). As shown in FIG. 8, both valves (210, 300) are in this state with cutter (50) advanced to position 1 such that lateral aperture (34) of needle (16) is closed.

In an eighth state, first valve (210) is in a vacuum state and second valve (300) is in a vent state. In this state, first valve spool (214) is rotated by a corresponding actuator (24) such that hole (218) is aligned with first connector (240) of first valve housing (212), as shown in FIG. 5B. Accordingly, vacuum from fourth tube (130) is in fluid communication with first tube (102) such that a lateral vacuum is supplied to second lumen (38) of needle (16) of biopsy device (10). It should be understood that in this orientation, hemi-cylindrical portion (222) of first valve spool (214) is positioned such that saline connector (190) is not in fluid communication with second connector (246) of first valve housing (212). Accordingly, saline from saline bag (50) and fifth tube (140) is not in fluid communication with third tube (106). Also in this state, second valve spool (314) is rotated by a corresponding actuator (24) such that hole (318) is aligned with second vent connector (350) of second valve housing (312) such that second tube (104) is in fluid communication with second vent (352), as shown in FIG. 6C. Accordingly, atmospheric air is supplied to cutter lumen (52) of cutter (50) such that axial venting is provided to biopsy device (10). As shown in FIG. 8, both valves (210, 300) are rotated into this state as cutter (50) is retracted to open lateral aperture (34) of needle (16). Both valves (210, 300) remain in this state such that a marker may be deployed to the biopsy site through lateral aperture (34) of needle (16) of biopsy device (10) after cutter (50) is retracted. Cutter (50) may then be advanced to reclose lateral aperture (34) of needle (16).

In a ninth state, first valve (210) is rotated to a vent position while second valve (300) remains at a vent position such that atmospheric pressure is provided to both first tube (102) and second tube (104). In this state, first valve spool (214) is rotated to the position shown in FIG. 5D and described above. Second valve spool (314) maintains the venting position such that hole (318) is aligned with second vent connector (350) of second valve housing (312) such that second tube (104) is in fluid communication with second vent (352), as shown in FIG. 6C. In this state, biopsy device (10) and tubes (102, 104) are vented to atmosphere to remove residual pressure therein. In some versions, first valve (210) and second valve (300) may be rotated back to the first state, the "dead head" state, described above, prior to a new biopsy sample acquisition. For example, as shown in FIG. 8, both first valve (210) and second valve (300) are rotated to the vent positions to relieve residual pressure followed by rotating to the "dead head" state.

Figure 9:
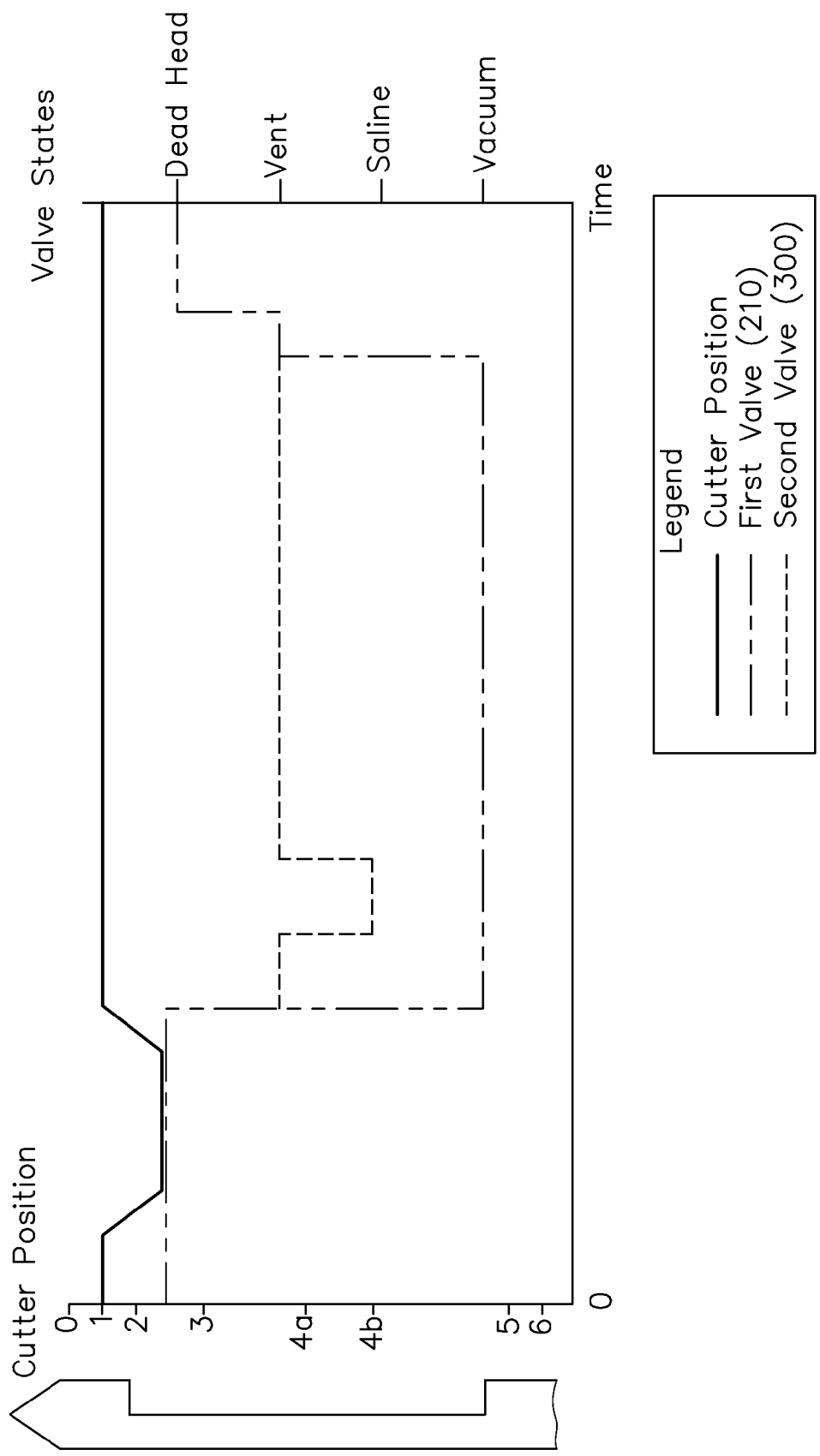
FIG. 9 depicts a graph view of yet another exemplary operational process showing exemplary states of the first valve and second valve relative to time and a cutter position.

In some instances, a clear probe algorithm may be initiated if tissue is jammed in cutter lumen (52) of cutter (50). By way of example only, an operator may determine that tissue is jammed in cutter lumen (52) if the operator completes a full cutting stroke with cutter (50) (e.g., in accordance with the process depicted in FIG. 7), yet a severed tissue sample does not appear within tissue sample holder (18). In the clear probe algorithm of the present example, as shown in FIG. 9, both first valve (210) and second valve (300) are in a "dead head" state during retraction and advancement of cutter (50) such that no fluid is provided through tubes (102, 104, 106). In this state, first valve spool (214) is rotated such that hole (218) is not aligned with either first connector (240) or first vent connector (250), as shown in FIG. 5A, such that first tube (102) is not in fluid communication with either vent (252) or fourth tube (130). In addition, first valve spool (214) is oriented such that hemi-cylindrical section (222) substantially blocks fluid transfer from second connector (246) to saline connector (190) such that saline from saline bag (50) is not delivered to third tube (106). In this state, second valve spool (314) is rotated such that hole (318) is not aligned with either connector (340) or second vent connector (350), as shown in FIG. 6A, such that second tube (104) is not in fluid communication with either vent (352) or fourth tube (130). Thus, valve assembly unit (100) provides substantially no fluids to biopsy device (10). It should be noted that cutter (50) is only retracted slightly before advancing again, as shown in FIG. 9. In some instances, the retraction of cutter (50) is so slight that cutter (50) will not sever an additional tissue sample as it is advanced again. In other words, cutter (50) does not effectively open lateral aperture (34) of needle (16) enough to allow tissue to protrude into lateral aperture (34) for severing by cutter (50).

After advancement of cutter (50) back to the distal-most position, first valve (210) is rotated to a vent position such that an atmospheric pressure is provided through first tube (102) while second valve (300) is rotated to a vacuum state such that a negative (vacuum) pressure is provided second tube (104). In this state, first valve spool (214) is rotated by a corresponding actuator (24) such that hole (218) is aligned with first vent connector (250) such that first tube (102) is in fluid communication with first vent (252), as shown in FIG. 5C. Second valve spool (314) remains in the position shown in FIG. 6B and described above such that an axial vacuum is provided through second tube (104). In this state, the previously severed tissue sample may continue to be drawn axially through biopsy device (10) towards tissue sample holder (18) or, in some versions, any tissue debris within needle (16) is cleared from therein via the axial vacuum.

First valve (210) is then rotated to a saline position such that saline is provided from saline bag (50) through first tube (102) while second valve (300) remains in a vacuum state such that a negative (vacuum) pressure is provided second tube (104). In this state, first valve spool (214) is rotated by a corresponding actuator (24) such that hemi-cylindrical portion (222) does not impede fluid flow from saline connector (190) to second connector (246) of first valve housing (212), as shown in FIG. 5D. Accordingly, saline from saline bag (50) and fifth tube (140) is in fluid communication biopsy device (10) via third tube (106). In this state, second valve spool (314) remains in the position shown in FIG. 6B and described above such that an axial vacuum is provided through second tube (104). Accordingly, the axial vacuum provided by second tube (104) is used in biopsy device (10) to draw saline through third tube (106) and to draw a severed tissue sample axially through cutter lumen (52) toward tissue sample holder (18). As shown in FIG. 9, first valve spool (214) may be rotated back to venting to atmosphere to alternate the supply of atmospheric air and saline to second lumen (38) of needle (16) of biopsy device (10). The alternation of saline and atmospheric air may be used to help flush a severed tissue sample into tissue sample holder (18) and/or clear biopsy device (10) of debris.

First valve (210) then remains in a vent position while second valve (300) is rotated to a vent position such that atmospheric pressure is provided to both first tube (102) and second tube (104). In this state, first valve spool (214) is in the position shown in FIG. 5D and described above. Second valve spool (314) is rotated by a corresponding actuator (24) such that hole (318) is aligned with second vent connector (350) of second valve housing (312) such that second tube (104) is in fluid communication with second vent (352), as shown in FIG. 6C. In this state, biopsy device (10) and tubes (102, 104) are vented to atmosphere to remove residual pressure therein. In some versions, first valve (210) and second valve (300) may be rotated back to the first state, the "dead head" state, described above, prior to a new biopsy sample acquisition. For example, as shown in FIG. 9, both first valve (210) and second valve (300) are rotated to the vent positions to relieve residual pressure followed by rotating to the "dead head" state.

Of course still further configurations and states will be apparent to one of ordinary skill in the art in view of the teachings herein. Moreover, it should be understood that the foregoing states are merely exemplary and may be applied in any order as will be apparent to one of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy system comprising:
   (a) a biopsy device, wherein the biopsy device comprises:
      (i) a body,
      (ii) a needle extending distally from the body, wherein the needle defines a lateral tissue receiving aperture, and
      (iii) a cutter translatable relative to the needle, wherein the cutter is configured to selectively close the lateral tissue receiving aperture of the needle;
   (b) a vacuum source;
   (c) a source of saline; and
   (d) a valve assembly in fluid communication with the needle of the biopsy device, wherein the valve assembly comprises:
      (i) a first valve comprising a first input port, a second input port, an exit port, and a vent port, wherein the first valve is operable to selectively provide atmospheric venting to the needle via the vent port, wherein the first valve is further operable to selectively provide vacuum to the needle via the first input port,
      (ii) a second valve comprising a first input port, an exit port, and a vent port, wherein the second valve is operable to selectively provide atmospheric venting to the needle via the vent port, wherein the second valve is operable to selectively provide vacuum to the needle via the first input port, and
      (iii) a single part integral conduit member, wherein the conduit member comprises a first conduit coupled with the vacuum source, and a second conduit coupled with the source of saline, wherein the conduit member comprises a first connector and a second connector disposed on opposing ends of the first conduit, respectively, wherein the first connector is coupled to the first input port of the first valve and the second connector is coupled to the first input port of the second valve such that the first conduit defines a continuous fluid path through the first connector and the second connector between the first and second valves, wherein the first conduit is operable to provide vacuum to the first and second valves, wherein the second conduit comprises a third connector coupled with the second input port of the first valve, wherein the second conduit is operable to provide saline to the first valve.

2. The biopsy system of claim 1, wherein the needle defines a first lumen and a second lumen, wherein the cutter is translatable within the first lumen of the needle, wherein the cutter defines a cutter lumen.

3. The biopsy system of claim 2, wherein the first valve is in fluid communication with the second lumen of the needle and the second valve is in fluid communication with the cutter lumen of the cutter.

4. The biopsy system of claim 3, wherein the valve assembly comprises a first actuator coupled with the first valve and a second actuator coupled with the second valve.

5. The biopsy system of claim 4, wherein the first and second actuators are configured to actuate the first and second valves in response to the position of the cutter.

6. The biopsy system of claim 5, wherein the first and second valves are configured to be sealed when the cutter is positioned to close the lateral tissue receiving aperture.

7. The biopsy system of claim 5, wherein the first and second valves are configured to provide vacuum to the needle when the cutter is translated to open the lateral tissue receiving aperture.

8. The biopsy system of claim 5, wherein the cutter is configured to translate from an open position to a closed position, wherein the cutter is configured to close the lateral tissue receiving aperture in the closed position.

9. The biopsy system of claim 8, wherein the first valve is configured to provide venting to the needle when the cutter is translated to the closed position, wherein the second valve is configured to provide vacuum to the needle when the cutter is translated to the closed position.

10. The biopsy system of claim 9, wherein the first valve is operable to selectively provide saline to the second lumen of the needle when the cutter is translated to the closed position, wherein the second valve is configured to provide vacuum to the cutter lumen of the cutter when the cutter is translated to the closed position.

11. The biopsy system of claim 8, wherein the first and second valves are configured to provide venting to the needle when the cutter is translated to the closed position.

12. The biopsy system of claim 8, wherein the first valve is configured to provide vacuum to the needle when the cutter is translated to open the lateral tissue receiving aperture, wherein the second valve is configured to provide venting to the needle when the cutter is translated to open the lateral tissue receiving aperture.

13. The biopsy system of claim 1, wherein the valve assembly comprises a luer connector, wherein the luer connector is operable to selectively couple the valve assembly with the biopsy device.

14. The biopsy system of claim 1 further comprising a control unit, wherein the control unit is operable to actuate the valve assembly.

15. The biopsy system of claim 14, wherein the control unit comprises a valve assembly receptacle, wherein the valve assembly receptacle is configured to receive a proximal end of the valve assembly.

16. The biopsy system of claim 14, wherein the vacuum source is positioned within the control unit.

17. The biopsy system of claim 1, wherein the body of the biopsy device comprises a probe and a holster that is configured to couple with the probe, wherein the biopsy device further comprises a tissue sample holder at a proximal portion of the body.

18. The biopsy system of claim 1, wherein the conduit member comprises a tubular member, wherein the first and second connectors extend transversely from the tubular member.

* * * * *